US012648975B2

(12) United States Patent
Fang et al.

(10) Patent No.: US 12,648,975 B2
(45) Date of Patent: Jun. 9, 2026

(54) *LACTOBACILLUS PLANTARUM* AGAINST *HELICOBACTER PYLORI* INFECTION, AND USE THEREOF

(71) Applicant: WECARE PROBIOTICS CO., LTD., Jiangsu (CN)

(72) Inventors: Shuguang Fang, Jiangsu (CN); Zhonghui Gai, Jiangsu (CN); Yao Dong, Jiangsu (CN); Junli Zhang, Jiangsu (CN); Jiayue Gu, Jiangsu (CN); Jianguo Zhu, Jiangsu (CN)

(73) Assignee: WECARE PROBIOTICS CO., LTD., Jiangsu (CN)

( * ) Notice: Subject to any disclaimer, the term of this patent is extended or adjusted under 35 U.S.C. 154(b) by 0 days.

(21) Appl. No.: 18/572,825

(22) PCT Filed: Jul. 18, 2022

(86) PCT No.: PCT/CN2022/106180

§ 371 (c)(1),
(2) Date: Dec. 21, 2023

(87) PCT Pub. No.: WO2023/124018

PCT Pub. Date: Jul. 6, 2023

(65) Prior Publication Data

US 2024/0350566 A1     Oct. 24, 2024

(30) Foreign Application Priority Data

Dec. 29, 2021    (CN) .......................... 202111636673.2

(51) Int. Cl.
*A61K 35/747*     (2015.01)
*A61P 31/04*     (2006.01)
*C12N 1/20*     (2026.01)
*C12R 1/25*     (2006.01)

(52) U.S. Cl.
CPC ............. *A61K 35/747* (2013.01); *A61P 31/04* (2018.01); *C12N 1/20* (2013.01); *C12R 2001/25* (2021.05)

(58) Field of Classification Search
None
See application file for complete search history.

(56) References Cited

U.S. PATENT DOCUMENTS

2020/0077692 A1     3/2020   Chen et al.

FOREIGN PATENT DOCUMENTS

| CN | 102174450 A | | 9/2011 | |
| CN | 106635894 A | * | 5/2017 | |
| CN | 110201004 A | * | 9/2019 | ........... A61K 35/747 |
| CN | 111548972 A | | 8/2020 | |
| CN | 112080444 A | | 12/2020 | |
| CN | 112080445 A | | 12/2020 | |
| CN | 112914103 A | | 6/2021 | |
| CN | 113980878 A | | 1/2022 | |
| CN | 114525231 A | * | 5/2022 | ........... A61K 35/747 |
| KR | 20030077895 A | | 10/2003 | |
| TW | 201016847 A | | 5/2010 | |
| TW | 201540833 A | | 11/2015 | |

OTHER PUBLICATIONS

Chen, X.H., et al. "Biological characteristics of Lactobacillus plantarum with antagonistic activity against Heliobacter pylori" Sci. Tech. Food Industry (2012) 33(2):195-198 [Abstract].
International Application No. PCT/CN2022/106180; International Search Report; Oct. 13, 2022.
Chinese Patent Applciation No. 202111636673.2; Office Action; Feb. 8, 2022.
Qi, S., et al., "Screening and Functional Study of Lactobacillus Plantarum for Inhibition of Mildew" Sci. Tech. Food Industry (2020) 45(3):1-7 [Abstract].

* cited by examiner

*Primary Examiner* — Oluwatosin A Ogunbiyi
(74) *Attorney, Agent, or Firm* — Robert C. Netter, Jr.; Dann, Dorfman, Herrell & Skillman

(57)     ABSTRACT

Provided are a *Lactobacillus plantarum* against *Helicobacter pylori* infection and the use thereof. The *Lactobacillus plantarum* against *Helicobacter pylori* infection is named *Lactobacillus plantarum* Lp05 and was deposited in the China General Microbiological Culture Collection Center on 9 Oct. 2021, with the deposit number CGMCC No. 23547. Further provided are a method for culturing the *Lactobacillus plantarum* against *Helicobacter pylori* infection and a product for inhibiting *Helicobacter pylori* infection. The *Lactobacillus plantarum* against *Helicobacter pylori* infection of the present application has good gastric acid resistance, inhibits the proliferation of *Helicobacter pylori*, and reduces the adhesion effect of *Helicobacter pylori* to gastric epithelial cells, thereby creating conditions for the eradication of *Helicobacter pylori*. The product for inhibiting *Helicobacter pylori* infection does not cause adverse reactions nor drug resistance of pathogenic bacteria.

5 Claims, 4 Drawing Sheets

Specification includes a Sequence Listing.

1

LACTOBACILLUS PLANTARUM AGAINST HELICOBACTER PYLORI INFECTION, AND USE THEREOF

This application is a § 371 application of PCT/CN2022/106180, filed Jul. 18, 2022, which claims priority to Chinese Patent Application No. 202111636673.2, filed on Dec. 29, 2021. The foregoing applications are incorporated by reference herein.

Incorporated herein by reference in its entirety is the Sequence Listing being concurrently submitted as a XML file named SeqList, created Dec. 20, 2023, and having a size of 3,305 bytes.

TECHNICAL FIELD

The present application belongs to the technical field of microorganisms and, in particular, relates to a *Lactobacillus plantarum* against *Helicobacter pylori* infection and use thereof.

BACKGROUND

*Helicobacter pylori* (Hp) was first discovered in 1982 by Australian scholars Marshall and Warren. At present, Hp is classified as a group 1 carcinogenic factor, and an Hp infection rate of a natural population exceeds 50% and tends to increase year by year.

Hp is a gram-negative microaerophilic *bacillus* colonized in a human gastric mucosa and is a major causative factor for chronic gastritis, peptic ulcer, gastric mucosa-associated lymphoid tissue lymphoma and gastric cancer. Studies have shown that Hp has an apparent correlation with the occurrence and development of gastric ulcer with 80% or more of gastric ulcers being caused by Hp infection. Gastric ulcer is a common clinical chronic digestive system disease, which has a long course, a high recurrence rate and is difficult to cure thoroughly. The eradication of Hp is the key to the treatment of gastric ulcer and can promote the cure of gastric ulcer and significantly reduce the recurrence rate of ulcer.

With the increase in type of medication, a course of treatment is prolonged, and related adverse reactions are also increased. Gastrointestinal adverse reactions such as diarrhea and bloating are especially the most common. Affected by the increase in drug resistance of Hp and the adverse reactions caused by drugs, an eradication rate of Hp decreases year by year with a main reason relating to the increase in drug resistance of Hp to antibacterial drug caused by many factors such as strain variation, secondary resistance, cross-resistance and cross infection between different strains. Moreover, an unstandardized combination of antibiotics has a related adverse effect on a gastrointestinal microecological system, destroying the microecological balance and microbial barrier in a gastrointestinal tract so that antibacterial drug-sensitive strains are gradually reduced and drug-resistant strains are increased in an intestinal tract, resulting in adverse reactions such as epigastric discomfort, abdominal pain, nausea, vomiting and diarrhea in some patients, which tends to increase.

Therefore, how to provide a product capable of inhibiting *Helicobacter pylori*, which neither increases the drug resistance of *Helicobacter pylori* nor causes an adverse reaction of a patient in a treatment process, thereby improving an effect of clinical treatment of *Helicobacter pylori*, has become an urgent problem to be solved.

SUMMARY

The present application provides a *Lactobacillus plantarum* against *Helicobacter pylori* infection and use thereof. A culture solution of the *Lactobacillus plantarum* can inhibit the growth of *Helicobacter pylori* and significantly reduces an adhesive force of *Helicobacter pylori* to SGC7901 cells, GES1 cells, AGS cells and MKN45 cells, having a great application prospect in preparing a product for inhibiting *Helicobacter pylori*.

In a first aspect, the present application provides a *Lactobacillus plantarum* against *Helicobacter pylori* infection. The *Lactobacillus plantarum* against *Helicobacter pylori* infection is named *Lactobacillus plantarum* Lp05 and deposited in the China General Microbiological Culture Collection Center on Oct. 9, 2021, with a deposit number CGMCC No. 23547, where the China General Microbiological Culture Collection Center is located at No. 3, No. 1 West Beichen Road, Chaoyang District, Beijing, China, 100101.

In the present application, the *Lactobacillus plantarum* is also referred to as Lactiplantibacillus *plantarum*.

In the present application, the *Lactobacillus plantarum* against *Helicobacter pylori* infection has good gastric acid resistance, can inhibit the growth and proliferation of *Helicobacter pylori* and significantly reduces an adhesive force of *Helicobacter pylori* to SGC7901 cells, GES1 cells, AGS cells and MKN45 cells, thereby creating conditions for the eradication of *Helicobacter pylori*. The *Lactobacillus plantarum* against *Helicobacter pylori* infection is used to prepare an inhibitor so that neither *Helicobacter pylori* has drug resistance nor an adverse reaction of a patient is caused in a treatment process and an environmental pollution caused by the use of an antibiotic can be avoided, having a broad application prospect.

In the present application, the *Lactobacillus plantarum* against *Helicobacter pylori* infection is derived from a fermented pickle sample, and the strain is subjected to sequencing and analysis. A 16S rDNA sequence of the strain is shown in SEQ ID No: 1. The sequence obtained through the sequencing is subjected to nucleic acid sequence alignment in GeneBank. The result shows that the strain is indeed *Lactobacillus plantarum*.

```
SEQ ID No: 1:
ACGGCACTGCTATAGATGCAGTCGAACGAACTCTGGTATTGATTGGTGCT

TGCATCATGATTTACATTTGAGTGAGTGGCGAACTGGTGAGTAACACGTG

GGAAACCTGCCCAGAAGCGGGGGATAACACCTGGAAACAGATGCTAATAC

CGCATAACAACTTGGACCGCATGGTCCGAGCTTGAAAGATGGCTTCGGCT

ATCACTTTTGGATGGTCCCGCGGCGTATTAGCTAGATGGTGGGGTAACGG

CTCACCATGGCAATGATACGTAGCCGACCTGAGAGGGTAATCGGCCACAT

TGGGACTGAGACACGGCCCAAACTCCTACGGGAGGCAGCAGTAGGGAATC

TTCCACAATGGACGAAAGTCTGATGGAGCAACGCCGCGTGAGTGAAGAAG

GGTTTCGGCTCGTAAAACTCTGTTGTTAAAGAAGAACATATCTGAGAGTA

ACTGTTCAGGTATTGACGGTATTTAACCAGAAAGCCACGGCTAACTACGT

GCCAGCAGCCGCGGTAATACGTAGGTGGCAAGCGTTGTCCGGATTTATTG

GGCGTAAAGCGAGCGCAGGCGGTTTTTTAAGTCTGATGTGAAAGCCTTCG

GCTCAACCGAAGAAGTGCATCGGAAACTGGGAAACTTGAGTGCAGAAGAG

GACAGTGGAACTCCATGTGTAGCGGTGAAATGCGTAGATATATGGAAGAA

CACCAGTGGCGAAGGCGGCTGTCTGGTCTGTAACTGACGCTGAGGCTCGA
```

-continued

```
AAGTATGGGTAGCAAACAGGATTAGATACCCTGGTAGTCCATACCGTAAA

CGATGAATGCTAAGTGTTGGAGGGTTTCCGCCCTTCAGTGCTGCAGCTAA

CGCATTAAGCATTCCGCCTGGGGAGTACGGCCGCAAGGCTGAAACTCAAA

GGAATTGACGGGGGCCCGCACAAGCGGTGGAGCATGTGGTTTAATTCGAA

GCTACGCGAAGAACCTTACCAGGTCTTGACATACTATGCAAATCTAAGAG

ATTAGACGTTCCCTTCGGGGACATGGATACAGGTGGTGCATGGTTGTCGT

CAGCTCGTGTCGTGAGATGTTGGGTTAAGTCCCGCAACGAGCGCAACCCT

TATTATCAGTTGCCAGCATTAAGTTGGGCACTCTGGTGAGACTGCCGGTG

ACAAACCGGAGGAAGGTGGGGATGACGTCAAATCATCATGCCCCTTATGA

CCTGGGCTACACACGTGCTACAATGGATGGTACAACGAGTTGCGAACTCG

CGAGAGTAAGCTAATCTCTTAAAGCCATTCTCAGTTCGGATTGTAGGCTG

CAACTCGCCTACATGAAGTCGGAATCGCTAGTAATCGCGGATCAGCATGC

CGCGGTGAATACGTTCCCGGGCCTTGTACACACCGCCCGTCACACCATGA

GAGTTTGTAACACCCAAAGTCGGTGGGGTAACCTTTTAGGAACCAGCCGC

CTAAGGTATCGA.
```

In a second aspect, the present application provides a method for culturing the *Lactobacillus plantarum* against *Helicobacter pylori* infection according to the first aspect, which includes the following steps:

inoculating the *Lactobacillus plantarum* against *Helicobacter pylori* infection in an MRS liquid medium, and culturing for a period of 18-24 h at a temperature of 30-37° C., wherein the temperature of culturing may be, for example, 30° C., 31° C., 32° C., 33° C., 34° C., 35° C., 36° C. or 37° C., and the period of culturing may be, for example, 18 h, 19 h, 20 h, 21 h, 22 h, 23 h or 24 h. Other specific point values within the numerical ranges may be selected, and details are not described here.

In a third aspect, the present application provides use of the *Lactobacillus plantarum* against *Helicobacter pylori* infection according to the first aspect for preparing a product for inhibiting *Helicobacter pylori* infection.

Preferably, a number of viable bacteria of the *Lactobacillus plantarum* against *Helicobacter pylori* infection in the product is not less than $1\times10^8$ CFU/mL or $1\times10^8$ CFU/g, which may be, for example, $1\times10^8$ CFU/mL, $2\times10^8$ CFU/mL, $3\times10^8$ CFU/mL, $4\times10^8$ CFU/mL, $5\times10^8$ CFU/mL, $6\times10^8$ CFU/mL, $7\times10^8$ CFU/mL, $8\times10^8$ CFU/mL or $9\times10^8$ CFU/mL, or $1\times10^8$ CFU/g, $2\times10^8$ CFU/g, $3\times10^8$ CFU/g, $4\times10^8$ CFU/g, $5\times10^8$ CFU/g, $6\times10^8$ CFU/g, $7\times10^8$ CFU/g, $8\times10^8$ CFU/g or $9\times10^8$ CFU/g. Other specific point values within the numerical ranges may be selected, and details are not described here.

Preferably, the product includes any one of a food, a health care product, a drug or a *Helicobacter pylori* inhibitor.

In a fourth aspect, the present application provides a health care product for inhibiting *Helicobacter pylori* infection. The health care product includes the *Lactobacillus plantarum* against *Helicobacter pylori* infection according to the first aspect.

Preferably, the health care product includes any one of a soy product, a dairy product or a fruit and vegetable product.

In a fifth aspect, the present application provides a *Helicobacter pylori* inhibitor. The *Helicobacter pylori* inhibitor includes the *Lactobacillus plantarum* against *Helicobacter pylori* infection according to the first aspect.

Preferably, the *Helicobacter pylori* inhibitor further includes a lyoprotectant.

Preferably, the lyoprotectant includes a skim milk powder solution, wherein the skim milk powder solution has a mass concentration of 8% to 12%, which may be, for example, 8%, 8.5%, 9%, 9.5%, 10%, 10.5%, 11%, 11.5% or 12%. Other specific point values within the numerical range may be selected, and details are not described here.

Preferably, a mass ratio of the lyoprotectant to the *Lactobacillus plantarum* against *Helicobacter pylori* infection is (1.8-2.3): 1, which may be, for example, 1.8:1, 1.9:1, 2:1, 2.1:1, 2.2:1 or 2.3:1. Other specific point values within the numerical range may be selected, and details are not described here.

Preferably, a number of viable bacteria of the *Lactobacillus plantarum* against *Helicobacter pylori* infection in the *Helicobacter pylori* inhibitor is not less than $1\times10^{10}$ CFU/mL or $1\times10^{10}$ CFU/g, which may be, for example, $1\times10^{10}$ CFU/mL, $2\times10^{10}$ CFU/mL, $3\times10^{10}$ CFU/mL, $4\times10^{10}$ CFU/mL, $5\times10^{10}$ CFU/mL, $6\times10^{10}$ CFU/mL, $7\times10^{10}$ CFU/mL, $8\times10^{10}$ CFU/mL or $9\times10^{10}$ CFU/mL, or $1\times10^{10}$ CFU/g, $2\times10^{10}$ CFU/g, $3\times10^{10}$ CFU/g, $4\times10^{10}$ CFU/g, $5\times10^{10}$ CFU/g, $6\times10^{10}$ CFU/g, $7\times10^{10}$ CFU/g, $8\times10^{10}$ CFU/g or $9\times10^{10}$ CFU/g. Other specific point values within the numerical ranges may be selected, and details are not described here.

Compared with the prior art, the present application has the beneficial effects below.

(1) In the present application, a strain of *Lactobacillus plantarum* against *Helicobacter pylori* infection is successfully screened out through plate coating and streaking purification. The *Lactobacillus plantarum* has good gastric acid resistance. After the *Lactobacillus plantarum* is incubated in artificial gastric juice with a pH of 2.0 for 3 h, a survival rate can reach 75.0% or more. After the *Lactobacillus plantarum* is incubated in artificial gastric juice with a pH of 2.5 for 3 h, the survival rate can reach 90.8% or more. After the *Lactobacillus plantarum* is incubated in artificial gastric juice with a pH of 3.0 for 3 h, the survival rate can reach 93.4% or more. A bacterial suspension and culture supernatant of the *Lactobacillus plantarum* both have a good inhibitory effect on *Helicobacter pylori*. After 48 h of culture, a diameter of an inhibition zone of the bacterial suspension of the *Lactobacillus plantarum* can reach 15.8±2.2 mm or more, and a diameter of an inhibition zone of the supernatant can reach 14.5±2 mm or more. After 72 h of culture, the diameter of the inhibition zone of the bacterial suspension of the *Lactobacillus plantarum* can reach 21.0±2.3 mm or more, and the diameter of the inhibition zone of the supernatant can reach 16.6±2.5 mm or more. Moreover, the adhesive force of *Helicobacter pylori* to the SGC7901 cells, the GES1 cells, the AGS cells and the MKN45 cells can be significantly reduced, and an adhesion rate is reduced to 70% or less of a control group, thereby providing a new idea for preparing a *Helicobacter pylori* inhibitor and a product for inhibiting *Helicobacter pylori* infection.

(2) The product containing the *Lactobacillus plantarum* against *Helicobacter pylori* infection has a good effect of inhibiting the growth of *Helicobacter pylori*. In the case of 48 h of culture, a diameter of an inhibition zone of a suspension of the health care product containing the *Lactobacillus plantarum* can reach 15.9±2.4 mm or more. In the case of 72 h of culture, the diameter of the inhibition zone of the suspension of the health care product containing the *Lactobacillus plantarum* can reach 21.2±2.2 mm or more. Moreover, *Helicobacter pylori* does not have drug resistance, an adverse reaction of a patient is not caused in a treatment process, and the ecological balance of microorganisms in a gastrointestinal tract of the patient is not destroyed, thereby creating conditions for the eradication of *Helicobacter pylori*. In addition, an environmental pollution caused by the abuse of an antibiotic can be avoided, and an application prospect is broad.

DETAILED DESCRIPTION

Figure 1:
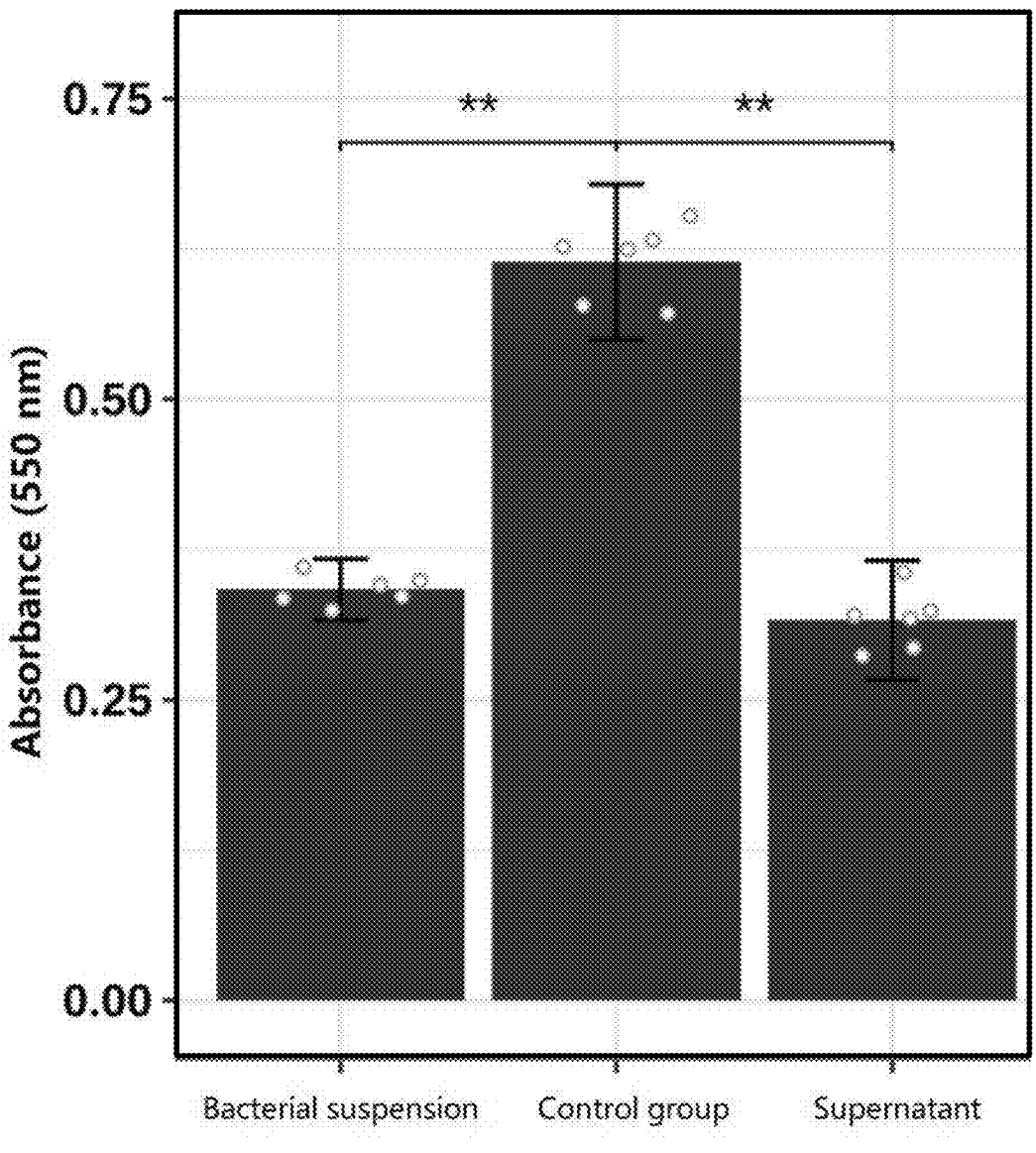
FIG. 1 is a diagram illustrating results of inhibiting an adhesion ability of *Helicobacter pylori* to gastric epithelial cells SGC7901 by *Lactobacillus plantarum*.

To further elaborate on the technical means adopted and effects achieved in the present application, the present application is further described below in conjunction with examples and drawings. It is to be understood that the specific examples set forth below are intended to explain the present application and not to limit the present application.

Experiments without specific techniques or conditions specified in the examples are conducted according to techniques or conditions described in the literature in the art or product specifications. The reagents or instruments used herein without manufacturers specified are conventional products commercially available from proper channels.

Materials and Methods

*Lactobacillus plantarum* against *Helicobacter pylori* infection was from a strain library of Wecare Probiotics (Suzhou) Co., Ltd. The strain is named *Lactobacillus plantarum* Lp05 and deposited in the China General Microbiological Culture Collection Center (CGMCC) on Oct. 9, 2021, with a deposit number CGMCC No. 23547, where the CGMCC is located at No. 3, NO. 1 West Beichen Road, Chaoyang District, Beijing 100101.

*Helicobacter pylori* was purchased from ATCC with a strain number ATCCA43504.

SGC7901 cells, GES1 cells, AGS cells and MKN45 cells were purchased from the Shanghai Cell Bank of the Chinese Academy of Sciences.

RPMI 1640 media were purchased from Wuhan Procell Life Science & Technology Co., Ltd.

Fetal bovine serum, PBS and trypsin were purchased from Thermo Fisher Scientific Inc.

Columbia media were purchased from OXOID Ltd. in the UK.

BHI media were purchased from Qingdao Hope Bio-Technology Co., Ltd.

MRS solid media: 10 g of peptone, 10 g of beef extract, 20 g of glucose, 2 g of sodium acetate, 5 g of yeast powder, 2 g of ammonium citrate dibasic, 2.6 g of $K_2PO_4\cdot3H_2O$, 0.1 g of $MgSO_4\cdot7H_2O$, 0.05 g of $MnSO_4$, 20 g of agar and 0.5 g of cysteine salt were weighed and dissolved in deionized water, 1 mL of polysorbate 80 was added, deionized water continued to be added until a total volume was 1 L, and after sterilization and cooling, the mixture was poured into a sterilized Petri dish for later use.

MRS liquid media: 10 g of peptone, 10 g of beef extract, 20 g of glucose, 2 g of sodium acetate, 5 g of yeast powder, 2 g of ammonium citrate dibasic, 2.6 g of $K_2PO_4\cdot3H_2O$, 0.1 g of $MgSO_4\cdot7H_2O$, 0.05 g of $MnSO_4$ and 0.5 g of cysteine salt were weighed and dissolved in deionized water, 1 mL of polysorbate 80 was added, deionized water continued to be added until a total volume was 1 L, and after sterilization and cooling, the mixture was for later use.

Example 1

In this example, strains against *Helicobacter pylori* infection were screened out from a fermented pickle. Steps are described below.

A fermented pickle sample was selected, subjected to 10-fold gradient dilution with normal saline having a mass concentration of 0.9% three times and coated on an MRS solid medium. After 48 h of culture at 37° C., typical colonies were picked and subjected to streaking purification on a surface of the MRS solid medium, and single colonies were picked, subjected to amplification culture in an MRS liquid medium at 37° C. and deposited in glycerol having a mass concentration of 30%.

The single colonies obtained through separation were screened according to abilities of the single colonies to inhibit the growth of *Helicobacter pylori*. Steps are described below.

(1) *Helicobacter pylori* at −80° C. was taken out, coated on a Columbia blood agar medium containing 5% sheep blood (v/v) for activation and culture and cultured in a microaerobic environment for 48 h at 37° C.

(2) The strains were inoculated in an MRS liquid medium and cultured for 18 h at 37° C. for activation two consecutive times to obtain an activation solution. The activation solution was inoculated in an MRS liquid medium at an inoculum volume of 2% (v/v) and cultured for 18 h at 37° C. to obtain a bacterial solution. The bacterial solution was centrifuged at 8000 g for 10 min, and supernatant was taken and passed through a 0.22 μm sterile filtration membrane to obtain supernatant. The strains were resuspended with PBS to obtain a bacterial suspension.

(3) Inhibition zone experiment

100 μL bacterial solution of *Helicobacter pylori* (with a density of $10^9$ CFU/mL) was coated onto a surface of a punctured Colombian blood agar medium (a volume of the medium was 20 mL) containing 5% sheep blood without an antibiotic, and any one of the following groups of liquids was added separately to form different experimental groups: 100 μL bacterial suspension to be tested, 100 μL supernatant to be tested, 100 μL positive control (a metronidazole solution having a mass concentration of 0.025%), 100 μL negative control (a PBS buffer) and a blank control (100 μL MRS liquid medium). Effects of inhibiting the growth of *Helicobacter pylori* at 48 h and 72 h by the strains were determined through an Oxford cup method, and the abilities of the strains to inhibit the growth of *Helicobacter pylori* were evaluated according to sizes of inhibition zones.

After the above operations, a strain with the best inhibitory ability to *Helicobacter pylori* was selected and identified.

Example 2

In this example, the strain screened in Example 1 was subjected to morphological identification and 16S rRNA molecular biological identification. Steps are described below.

(1) Morphological Identification

The strain was inoculated in an MRS solid medium, cultured for 48 h at 37° C. and observed under a microscope.

As can be seen from the observation, the colony was milky white and presented as a semicircular protrusion with a smooth and wet surface and a neat edge.

(2) 16S rRNA Molecular Biological Identification

The strain deposited at −80° C. was taken out, inoculated in an MRS liquid medium and cultured for 18 h at 37° C. 1 mL bacterial solution was pipetted to a centrifuge tube and centrifuged at 8000 rpm for 10 min. Supernatant was removed, and the strains were collected.

A genome of the strain was extracted, a general primer for bacteria was added for PCR amplification, and an amplification product was sent to Sangon Biotech (Shanghai) Co., Ltd. for sequencing and identification.

The strain was subjected to sequencing and analysis. A 16S rDNA sequence of the strain is shown in SEQ ID No: 1.

```
SEQ ID No: 1:
ACGGCACTGCTATAGATGCAGTCGAACGAACTCTGGTATTGATTGGTGCT

TGCATCATGATTTACATTTGAGTGAGTGGCGAACTGGTGAGTAACACGTG

GGAAACCTGCCCAGAAGCGGGGGATAACACCTGGAAACAGATGCTAATAC

CGCATAACAACTTGGACCGCATGGTCCGAGCTTGAAAGATGGCTTCGGCT

ATCACTTTTGGATGGTCCCGCGGCGTATTAGCTAGATGGTGGGGTAACGG

CTCACCATGGCAATGATACGTAGCCGACCTGAGAGGGTAATCGGCCACAT

TGGGACTGAGACACGGCCCAAACTCCTACGGGAGGCAGCAGTAGGGAATC

TTCCACAATGGACGAAAGTCTGATGGAGCAACGCCGCGTGAGTGAAGAAG

GGTTTCGGCTCGTAAAACTCTGTTGTTAAAGAAGAACATATCTGAGAGTA

ACTGTTCAGGTATTGACGGTATTTAACCAGAAAGCCACGGCTAACTACGT

GCCAGCAGCCGCGGTAATACGTAGGTGGCAAGCGTTGTCCGGATTTATTG

GGCGTAAAGCGAGCGCAGGCGGTTTTTTAAGTCTGATGTGAAAGCCTTCG

GCTCAACCGAAGAAGTGCATCGGAAACTGGGAAACTTGAGTGCAGAAGAG

GACAGTGGAACTCCATGTGTAGCGGTGAAATGCGTAGATATATGGAAGAA

CACCAGTGGCGAAGGCGGCTGTCTGGTCTGTAACTGACGCTGAGGCTCGA

AAGTATGGGTAGCAAACAGGATTAGATACCCTGGTAGTCCATACCGTAAA

CGATGAATGCTAAGTGTTGGAGGGTTTCCGCCCTTCAGTGCTGCAGCTAA

CGCATTAAGCATTCCGCCTGGGGAGTACGGCCGCAAGGCTGAAACTCAAA

GGAATTGACGGGGGCCCGCACAAGCGGTGGAGCATGTGGTTTAATTCGAA

GCTACGCGAAGAACCTTACCAGGTCTTGACATACTATGCAAATCTAAGAG

ATTAGACGTTCCCTTCGGGGACATGGATACAGGTGGTGCATGGTTGTCGT

CAGCTCGTGTCGTGAGATGTTGGGTTAAGTCCCGCAACGAGCGCAACCCT

TATTATCAGTTGCCAGCATTAAGTTGGGCACTCTGGTGAGACTGCCGGTG

ACAAACCGGAGGAAGGTGGGGATGACGTCAAATCATCATGCCCCTTATGA
```

-continued

```
CCTGGGCTACACACGTGCTACAATGGATGGTACAACGAGTTGCGAACTCG

CGAGAGTAAGCTAATCTCTTAAAGCCATTCTCAGTTCGGATTGTAGGCTG

CAACTCGCCTACATGAAGTCGGAATCGCTAGTAATCGCGGATCAGCATGC

CGCGGTGAATACGTTCCCGGGCCTTGTACACACCGCCCGTCACACCATGA

GAGTTTGTAACACCCAAAGTCGGTGGGGTAACCTTTTAGGAACCAGCCGC

CTAAGGTATCGA.
```

Example 3

The sequence obtained through the sequencing was subjected to nucleic acid sequence alignment in GeneBank. The result shows that the strain is *Lactobacillus plantarum*.

Based on the results of the 16S rRNA molecular biological identification and the morphological identification in Example 2, it is confirmed that the strain belongs to *Lactobacillus plantarum*, which is named *Lactobacillus plantarum* Lp05. The *Lactobacillus plantarum* is deposited in the China General Microbiological Culture Collection Center (CGMCC) on Oct. 9, 2021, with the deposit number CGMCC No. 23547, where the CGMCC is located at No. 3, NO. 1 West Beichen Road, Chaoyang District, Beijing 100101.

Example 4

In this example, optimal culture conditions for the *Lactobacillus plantarum* in Example 3 were determined. Steps are described below.

The *Lactobacillus plantarum* was inoculated in an MRS liquid medium and separately cultured for 48 h at 10-50° C., and in a culture process, OD600 values of a culture solution were measured with a microplate reader at intervals.

The results show that the *Lactobacillus plantarum* grows optimally at 30-37° C. and can be in a growth stabilization period after 18-24 h of culture.

Example 5

In this example, gastric acid resistance of the *Lactobacillus plantarum* in Example 3 was verified. Steps are described below.

(1) Preparation of Artificial Gastric Juice

The artificial gastric juice contained 0.20% NaCl and 0.30% pepsin in mass fraction, a pH was separately adjusted to 2.0, 2.5 and 3.0 by HCl, and the mixture was filtered and sterilized for later use.

(2) Gastric Acid Resistance Test 1.0 mL bacterial suspension of the *Lactobacillus plantarum* (with a concentration of $1\times10^9$ CFU/mL, where the concentration of the bacterial solution was measured through a method in a national standard GB4789.35-2016 National Food Safety Standard-Microbiological Examination of Food—Examination of Lactic Acid Bacteria) was separately mixed with 9.0 mL artificial gastric juice with a pH of 2.0, 2.5 and 3.0 and subjected to anaerobic standing culture at 37° C., samples were taken at the beginning (0 h) and 3 h after treatment, respectively, the number of viable bacteria was measured through a pouring culture method, and a survival rate of the viable bacteria was calculated. A formula is as follows:

$$\text{survival rate } (\%) = N1/N0 \times 100\%,$$

N1: the number of viable bacteria 3 h after the treatment of the artificial gastric juice; N0: the number of viable bacteria at 0 h.

The test results are shown in Table 1.

TABLE 1

| pH of Artificial Gastric Juice | Number of Viable Bacteria N0 (0 h) | Number of Viable Bacteria N1 (3 h) | Survival Rate (%) |
|---|---|---|---|
| 2.0 | $(5.20 \pm 0.40) \times 10^8$ | $(3.90 \pm 0.18) \times 10^8$ | 75.0 |
| 2.5 | $(5.20 \pm 0.40) \times 10^8$ | $(4.72 \pm 0.26) \times 10^8$ | 90.8 |
| 3.0 | $(5.20 \pm 0.40) \times 10^8$ | $(4.86 \pm 0.39) \times 10^8$ | 93.4 |

As can be seen from Table 1, the *Lactobacillus plantarum* in the present application has good gastric acid resistance. After the *Lactobacillus plantarum* is incubated in the artificial gastric juice with a pH of 2.0 for 3 h, the survival rate can reach 75.0% or more. After the *Lactobacillus plantarum* is incubated in the artificial gastric juice with a pH of 2.5 for 3 h, the survival rate can reach 90.8% or more. After the *Lactobacillus plantarum* is incubated in the artificial gastric juice with a pH of 3.0 for 3 h, the survival rate can reach 93.4% or more. The good acid resistance creates conditions for preparing a *Helicobacter pylori* inhibitor from the *Lactobacillus plantarum*.

Example 6

In this example, an inhibitory effect of the *Lactobacillus plantarum* in Example 3 on the growth of *Helicobacter pylori* was verified. Steps are described below.

(1) *Helicobacter pylori* at −80° C. was taken out, coated on a Columbia blood agar medium containing 5% sheep blood (v/v) for activation and culture and cultured in a microaerobic environment for 48 h at 37° C.

(2) The *Lactobacillus plantarum* was inoculated in an MRS liquid medium and cultured for 18 h at 37° C. for activation two consecutive times to obtain an activation solution. The activation solution was inoculated in an MRS liquid medium at an inoculum volume of 2% (v/v) and cultured for 18 h at 37° C. to obtain a bacterial solution. The bacterial solution was centrifuged at 8000 g for 10 min, and supernatant was taken and passed through a 0.22 μm sterile filtration membrane to obtain supernatant of the *Lactobacillus plantarum*. The strains were resuspended with PBS to obtain a bacterial suspension of the *Lactobacillus plantarum*.

(3) Inhibition zone experiment

100 μL bacterial solution of *Helicobacter pylori* (with a density of $10^9$ CFU/mL) was coated onto a surface of a punctured Colombian blood agar medium (a volume of the medium was 20 mL) containing 5% sheep blood without an antibiotic, and any one of the following groups of liquids was added separately to form different experimental groups: 100 μL bacterial suspension of the *Lactobacillus plantarum* to be tested, 100 μL supernatant of the *Lactobacillus plantarum* to be tested, 100 μL positive control (a metronidazole solution having a mass concentration of 0.025%), 100 μL negative control (a PBS buffer) and a blank control (100 μL MRS liquid medium). Effects of inhibiting the growth of *Helicobacter pylori* at 48 h and 72 h by the *Lactobacillus plantarum* were determined through the Oxford cup method. The results are shown in Table 2.

TABLE 2

| | Diameter of Inhibition Zone at 48 h (mm) | Diameter of Inhibition Zone at 72 h (mm) |
|---|---|---|
| Bacterial suspension of *Lactobacillus plantarum* | 15.8 ± 2.2 | 21.0 ± 2.3 |
| Supernatant of *Lactobacillus plantarum* | 14.5 ± 2 | 16.6 ± 2.5 |
| Positive control | 11.2 ± 2.3 | 12.4 ± 3.1 |
| Negative control | 0 | 0 |
| Blank control | 0 | 0 |

As can be seen from Table 2, the MRS liquid medium has no inhibitory effect on *Helicobacter pylori*, and the bacterial suspension and supernatant of the *Lactobacillus plantarum* both have an inhibitory effect on the growth of *Helicobacter pylori*. In the case of 48 h of culture, a diameter of an inhibition zone of the bacterial suspension of the *Lactobacillus plantarum* can reach 15.8±2.2 mm or more, and a diameter of an inhibition zone of the supernatant can reach 14.5±2 mm or more. In the case of 72 h of culture, the diameter of the inhibition zone of the bacterial suspension of the *Lactobacillus plantarum* can reach 21.0±2.3 mm or more, and the diameter of the inhibition zone of the supernatant can reach 16.6±2.5 mm or more. A bacteriostatic effect is apparent, and the *Lactobacillus plantarum* can be applied to the preparation of a *Helicobacter pylori* inhibitor.

Example 7

In this example, effects of inhibiting adhesion abilities of *Helicobacter pylori* to gastric epithelial cells SGC7901, GES1, AGS and MKN45 by the *Lactobacillus plantarum* in Example 3 were verified. Steps are described below.

(1) Culture of Cells

① Cell Revival

Frozen storage tubes each containing 1 mL cell suspension were rapidly thawed in a water bath at 37° C., and 4 mL RPMI 1640 medium containing 10% fetal bovine serum was added and mixed uniformly. The mixtures were centrifuged at 1000 rmp for 3 min, supernatant was discarded, 2 mL RPMI 1640 medium containing 10% fetal bovine serum was added and mixed uniformly, and all cell suspensions were added to culture flasks for culture.

② Cell Passage

In the case where a cell density reached 80% or more, subculture was performed.

Culture supernatant was discarded, and the cells were rinsed twice with PBS.

1 mL digestive juice (0.25% trypsin and 0.53 mM EDTA) was added to each of the culture flasks, placed in an incubator at 37° C. and digested for 2 min.

A medium was added in 7 mL/flask, blown gently and uniformly, pipetted and centrifuged at 1000 rmp for 3 min, supernatant was discarded, and 2 mL culture solution was added and mixed uniformly.

The cell suspensions were inoculated in new culture flasks each containing 8 mL medium at a ratio of 1:2.

(2) Preparation of Strains of *Helicobacter pylori*

*Helicobacter pylori* was subjected to streaking on a surface of a Colombian blood solid medium (39 g solid powder of a Colombian medium was dissolved in 1 L water, sterilized for 15 min at 121° C. and cooled to 55° C., and sterile defibrinated sheep blood having a volume fraction of 7.5% was added, mixed uniformly and poured into a sterilized Petri dish for later use) and cultured in a three-gas incubator (85% $N_2$, 10% $CO_2$ and 5% $O_2$) for 3 days at 37°

C. to obtain single colonies. Single colonies were picked, inoculated in a BHI medium containing 5% fetal bovine serum and cultured in the three-gas incubator for 4 days at 37° C. to obtain a seed solution. The seed solution was cultured in a BHI medium at an inoculum volume of 2% and cultured in the three-gas incubator for 4 days at 37° C. to obtain a bacterial solution of *Helicobacter pylori*. The bacterial solution of *Helicobacter pylori* was centrifuged at 8000 g for 10 min to obtain the strains of *Helicobacter pylori*.

(3) Preparation of Strains of the *Lactobacillus plantarum*

The *Lactobacillus plantarum* was inoculated in an MRS liquid medium and cultured for 18 h at 37° C. for activation two consecutive times to obtain an activation solution. The activation solution was inoculated in an MRS liquid medium at an inoculum volume of 2% (v/v) and cultured for 18 h at 37° C. to obtain a bacterial solution. The bacterial solution was centrifuged at 8000 g for 10 min to obtain the strains of the *Lactobacillus plantarum*.

(4) Adhesion Inhibition Experiment

The strains of *Helicobacter pylori* were resuspended with PBS to a concentration of $1 \times 10^8$ CFU/mL to obtain a bacterial suspension of *Helicobacter pylori*. The strains of the *Lactobacillus plantarum* were resuspended with PBS to a concentration of $1 \times 10^8$ CFU/mL to obtain a bacterial suspension of the *Lactobacillus plantarum*. 1 mL bacterial suspension of *Helicobacter pylori* was separately mixed with 1 mL bacterial suspension of the *Lactobacillus plantarum* and 1 mL culture supernatant of the *Lactobacillus plantarum* and added to the SGC7901 cells, the GES1 cells, the AGS cells and the MKN45 cells, respectively, while control groups (1 mL bacterial suspension of *Helicobacter pylori* was mixed with 1 mL PBS solution) were set and subjected to the same operations, and the cells were cultured for 2 h under conditions of 37° C. and 5% $CO_2$. After washing three times with PBS, urease media (each containing 0.9% of NaCl, 7.2% of PBS, 20 mM of urea and 14 μg/mL of phenol red) were added and cultured for 1 h, and absorbance values were measured at a wavelength of 550 nm with a microplate reader. The urease activity of *H. pylori* characterized the adhesion abilities of *Helicobacter pylori*.

Figure 2:
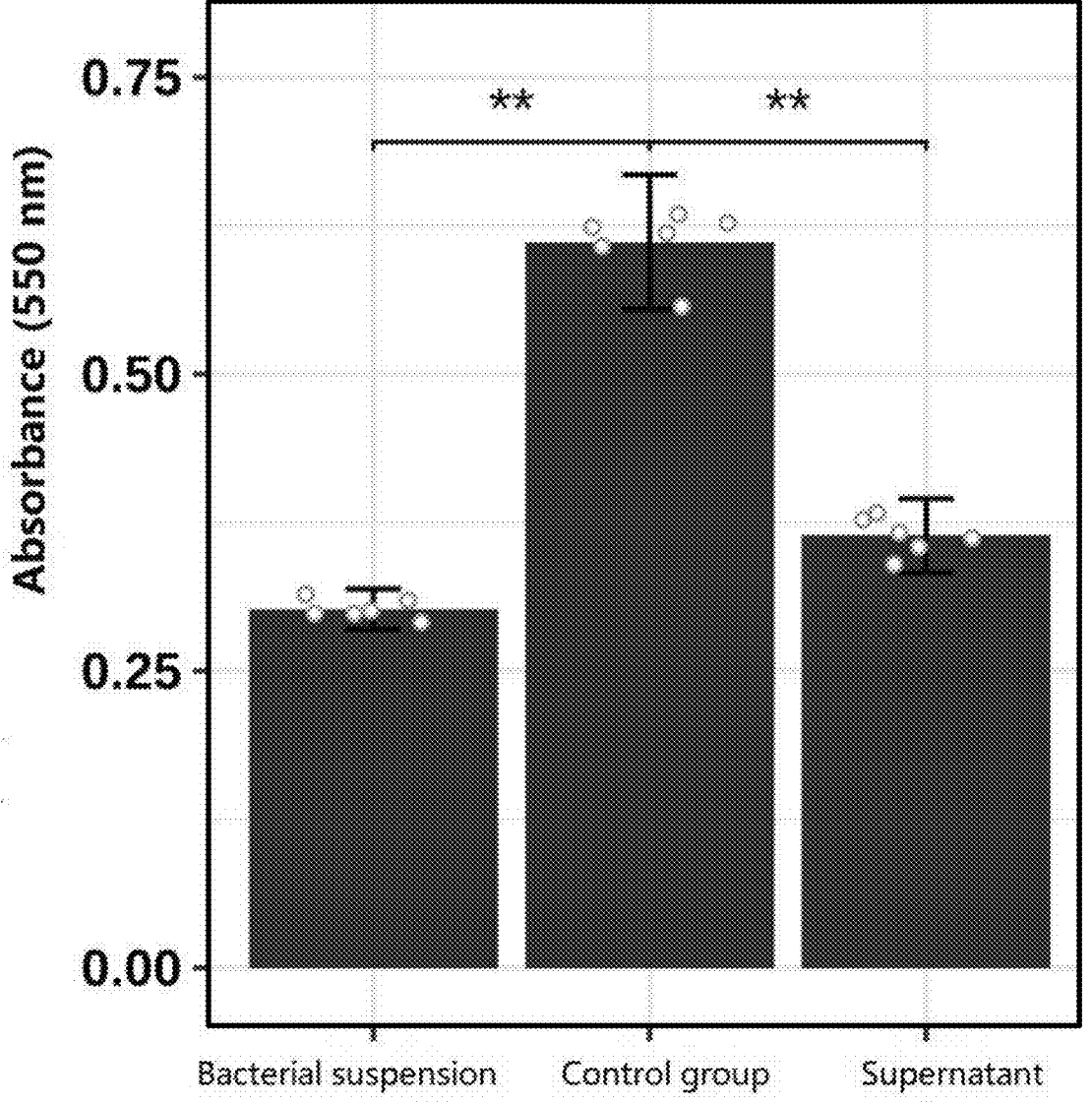
FIG. 2 is a diagram illustrating results of inhibiting an adhesion ability of *Helicobacter pylori* to gastric epithelial cells GES1 by *Lactobacillus plantarum*.
Figure 3:
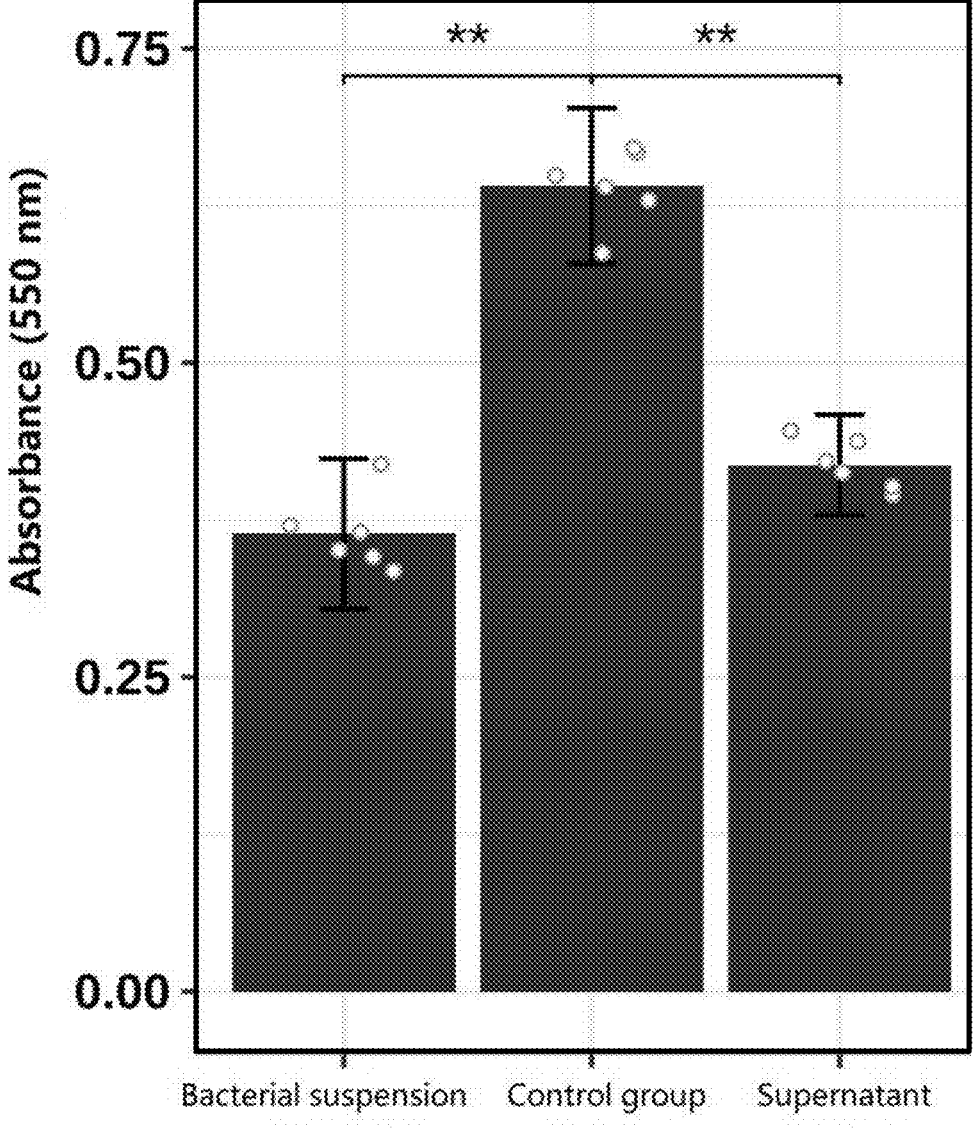
FIG. 3 is a diagram illustrating results of inhibiting an adhesion ability of *Helicobacter pylori* to gastric epithelial cells AGS by *Lactobacillus plantarum*.
Figure 4:
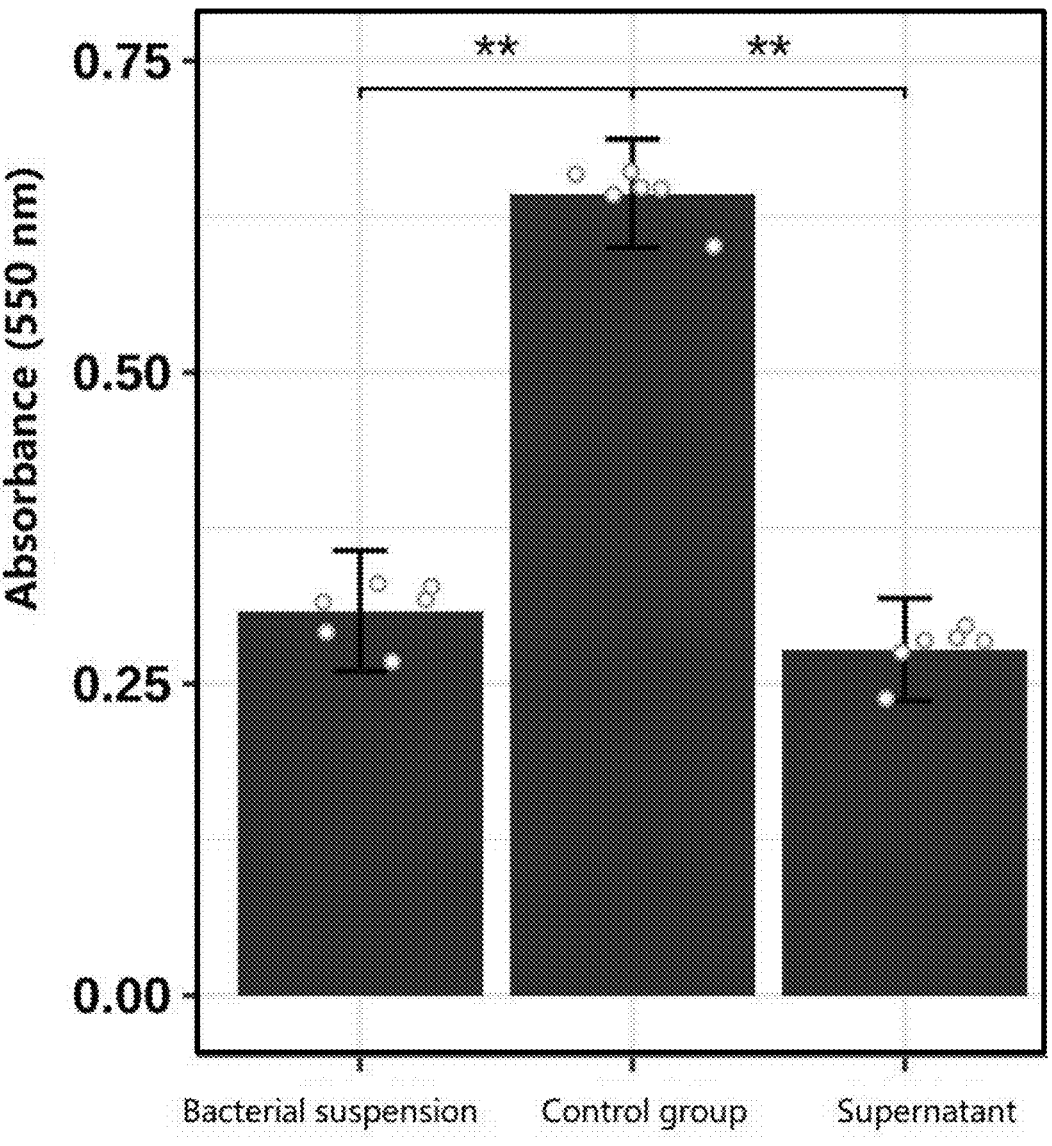
FIG. 4 is a diagram illustrating results of inhibiting an adhesion ability of *Helicobacter pylori* to gastric epithelial cells MKN45 by *Lactobacillus plantarum*.

The detection results of the adhesion abilities of *Helicobacter pylori* to the SGC7901 cells, the GES1 cells, the AGS cells and the MKN45 cells are shown in FIGS. 1, 2, 3 and 4, respectively.

As can be seen from the figures, compared with the control groups, after the bacterial suspensions or culture supernatant of the *Lactobacillus plantarum* is added, the adhesion abilities of *Helicobacter pylori* to the SGC7901 cells, the GES1 cells, the AGS cells and the MKN45 cells are all significantly reduced, and the adhesion rates to the four types of cells are all reduced to 70% or less of the control groups, indicating that the *Lactobacillus plantarum* can reduce an adhesion ability of *Helicobacter pylori* to gastric epithelial cells, thereby creating conditions for the eradication of *Helicobacter pylori*.

Example 8

This example provides a *Helicobacter pylori* inhibitor. The *Helicobacter pylori* inhibitor was prepared through the method described below.

*Lactobacillus plantarum* was inoculated in an MRS liquid medium and cultured for 24 h at 37° C. for activation two consecutive times to obtain an activation solution. The activation solution was inoculated in an MRS liquid medium at an inoculum volume of 2% (v/v) and cultured for 24 h at 37° C. to obtain a bacterial solution. The bacterial solution was centrifuged at 8000 g for 10 min to obtain strains of the *Lactobacillus plantarum*.

The strains were resuspended with skim milk powder having a mass concentration of 10% to a concentration of $1 \times 10^{10}$ CFU/mL to obtain a bacterial suspension. The bacterial suspension was pre-cultured for 1 h at 37° C. and lyophilized to obtain the *Helicobacter pylori* inhibitor.

Example 9

This example provides a health care product for inhibiting *Helicobacter pylori* infection. The health care product for inhibiting *Helicobacter pylori* infection includes 0.1 g of lyophilized powder of a *Lactobacillus plantarum* against *Helicobacter pylori* infection and 1.9 g of inulin, which can be made into a pouch product for brewing.

Calculated according to 2.0 g per pouch, the product contains 2 billion of CFU probiotics per pouch. Inulin is a prebiotic, and the health care product prepared through a combination of *Lactobacillus plantarum* Lp05 and inulin can be synergistic to each other, which is conducive to preventing and treating *Helicobacter pylori* infection.

A preparation method of the lyophilized powder of the *Lactobacillus plantarum* against *Helicobacter pylori* infection is described below.

*Lactobacillus plantarum* Lp05 was inoculated in an MRS liquid medium at an inoculum volume of 3% of a total mass of the medium and cultured for 18 h at 37° C. to obtain a culture solution. The culture solution was centrifuged at 8000 g for 10 min to obtain strains. The strains were mixed with a skim milk powder solution to obtain a resuspension, where the skim milk powder solution had a mass concentration of 10%, and a mass ratio of skim milk powder to strains was 2:1. The resuspension was lyophilized through a vacuum freezing method to obtain the lyophilized powder of *Lactobacillus plantarum* Lp05.

The health care product for inhibiting *Helicobacter pylori* infection was prepared into a suspension (a density of *Lactobacillus plantarum* Lp05 was $10^9$ CFU/mL) with water, 100 μL suspension was taken and coated onto a surface of a punctured Colombian blood agar medium (a volume of the medium was 20 mL) containing 5% sheep blood without an antibiotic, and any one of the following groups of liquids was added separately to form different experimental groups: 100 μL suspension of the health care product to be tested, 100 μL positive control (a metronidazole solution having a mass concentration of 0.025%), 100 μL negative control (a PBS buffer) and a blank control (100 μL MRS liquid medium). Effects of inhibiting the growth of *Helicobacter pylori* at 48 h and 72 h were determined through an Oxford cup method. The results are shown in Table 3.

TABLE 3

| | Diameter of Inhibition Zone at 48 h (mm) | Diameter of Inhibition Zone at 72 h (mm) |
|---|---|---|
| Suspension of health care product containing *Lactobacillus plantarum* Lp05 | 15.9 ± 2.4 | 21.2 ± 2.2 |
| Positive control | 9.3 ± 2.5 | 9.8 ± 2.5 |
| Negative control | 0 | 0 |
| Blank control | 0 | 0 |

As can be seen from Table 3, the suspension of the health care product containing *Lactobacillus plantarum* Lp05 has an inhibitory effect on the growth of *Helicobacter pylori*. In the case of 48 h of culture, a diameter of an inhibition zone of the suspension of the health care product containing the *Lactobacillus plantarum* can reach 15.9±2.4 mm or more. In the case of 72 h of culture, the diameter of the inhibition zone of the suspension of the health care product containing the *Lactobacillus plantarum* can reach 21.2±2.2 mm or more. A bacteriostatic effect is apparent, and the health care product containing the *Lactobacillus plantarum* has practical application value.

In conclusion, the present application provides the *Lactobacillus plantarum* against *Helicobacter pylori* infection, which has the good gastric acid resistance, can inhibit the proliferation of *Helicobacter pylori* and reduces the adhesion of *Helicobacter pylori* to multiple gastric epithelial cells, thereby creating conditions for the eradication of *Helicobacter pylori*, and the *Lactobacillus plantarum* against *Helicobacter pylori* infection is prepared into a corresponding product for inhibiting *Helicobacter pylori* infection so that neither an adverse reaction is caused nor the balance of flora of microorganisms in an intestinal tract is affected and that pathogenic bacteria such as *Helicobacter pylori* have drug resistance due to the use of antibiotics is avoided, having value in practical production.

The applicant has stated that although the detailed method of the present application is described through the examples described above, the present application is not limited to the detailed method described above, which means that the implementation of the present application does not necessarily depend on the detailed method described above. It should be apparent to those skilled in the art that any improvements made to the present application, equivalent replacements of raw materials of the product of the present application, additions of adjuvant ingredients, selections of specific manners, etc., all fall within the protection scope and the disclosure scope of the present application.

What is claimed is:

1. A method for culturing a *Lactobacillus plantarum* against *Helicobacter pylori* infection, comprising:

inoculating the *Lactobacillus plantarum* against *Helicobacter pylori* infection in an MRS liquid medium, and culturing for 18-24 h at 30-37° C., wherein the *Lactobacillus plantarum* against *Helicobacter pylori* infection is named *Lactobacillus plantarum* Lp05 and deposited in the China General Microbiological Culture Collection Center on Oct. 9, 2021, with a deposit number CGMCC No. 23547.

2. A *Helicobacter pylori* inhibitor, comprising a *Lactobacillus plantarum* against *Helicobacter pylori* infection, which is named *Lactobacillus plantarum* Lp05 and deposited in the China General Microbiological Culture Collection Center on Oct. 9, 2021, with a deposit number CGMCC No. 23547, wherein the *Helicobacter pylori* inhibitor further comprises a lyoprotectant;

wherein the lyoprotectant comprises a skim milk powder solution, wherein the skim milk powder solution has a mass concentration of 8% to 12%; and a mass ratio of the lyoprotectant to the *Lactobacillus plantarum* against *Helicobacter pylori* infection is (1.8-2.3):1.

3. The *Helicobacter pylori* inhibitor according to claim 2, wherein a number of viable bacteria of the *Lactobacillus plantarum* against *Helicobacter pylori* infection in the *Helicobacter pylori* inhibitor is not less than $1\times10^{10}$ CFU/mL or $1\times10^{10}$ CFU/g.

4. A method for inhibiting *Helicobacter pylori* infection, comprising administering an effective amount of a product containing the *Lactobacillus plantarum* against *Helicobacter pylori* infection to subject in need thereof, wherein the *Lactobacillus plantarum* against *Helicobacter pylori* infection is named *Lactobacillus plantarum* Lp05 and deposited in the China General Microbiological Culture Collection Center on Oct. 9, 2021, with a deposit number CGMCC No. 23547.

5. The method according to claim 4, wherein a number of viable bacteria of the *Lactobacillus plantarum* against *Helicobacter pylori* infection in the product is not less than $1 \times 10^8$ CFU/mL or $1 \times 10^8$ CFU/g; and the product comprises any one of a food, a health care product, a drug or a *Helicobacter pylori* inhibitor.

\* \* \* \* \*

```
                          SEQUENCE LISTING

Sequence total quantity: 1
SEQ ID NO: 1            moltype = DNA  length = 1462
FEATURE                Location/Qualifiers
source                 1..1462
                       mol_type = genomic DNA
                       organism = Lactobacillus plantarum
SEQUENCE: 1
acggcactgc tatagatgca gtcgaacgaa ctctggtatt gattggtgct tgcatcatga  60
tttacatttg agtgagtggc gaactggtga gtaacacgtg ggaaacctgc ccagaagcgg  120
gggataacac ctggaaacag atgctaatac cgcataacaa cttggaccgc atggtccgag  180
cttgaaagat ggcttcggct atcacttttg gatggtcccg cggcgtatta gctagatggt  240
ggggtaacgg ctcaccatgg caatgatacg tagccgacct gagagggtaa tcggccacat  300
tgggactgag acacggccca aactcctacg ggaggcagca gtagggaatc ttccacaatg  360
gacgaaagtc tgatggagca acgccgcgtg agtgaagaag ggtttcggct cgtaaaactc  420
tgttgttaaa gaagaacata tctgagagta actgttcagg tattgacggt atttaaccag  480
aaagccacgg ctaactacgt gccagcagcc gcggtaatac gtaggtggca agcgttgtcc  540
ggatttattg ggcgtaaagc gagcgcaggc ggtttttaa gtctgatgtg aaagccttcg  600
gctcaaccga agaagtgcat cggaaactgg gaaacttgag tgcagaagag gacagtggaa  660
ctccatgtgt agcggtgaaa tgcgtagata tatggaagaa caccagtggc gaaggcggct  720
gtctggtctg taactgacgc tgaggctcga aagtatgggt agcaaacagg attagatacc  780
ctggtagtcc ataccgtaaa cgatgaatgc taagtgttgg agggtttccg cccttcagtg  840
ctgcagctaa cgcattaagc attccgcctg gggagtacgg ccgcaaggct gaaactcaaa  900
ggaattgacg ggggcccgca caagcggtgg agcatgtggt ttaattcgaa gctacgcgaa  960
gaaccttacc aggtcttgac atactatgca aatctaagag attagacgtt cccttcgggg  1020
acatggatac aggtggtgca tggttgtcgt cagctcgtgt cgtgagatgt tgggttaagt  1080
cccgcaacga gcgcaaccct tattatcagt tgccagcatt aagttgggca ctctggtgag  1140
actgccggtg acaaaccgga ggaaggtggg gatgacgtca aatcatcatg ccccttatga  1200
cctgggctac acacgtgcta caatggatgg tacaacgagt tgcgaactcg cgagagtaag  1260
ctaatctctt aaagccattc tcagttcgga ttgtaggctg caactcgcct acatgaagtc  1320
ggaatcgcta gtaatcgcgg atcagcatgc cgcggtgaat acgttcccgg gccttgtaca  1380
caccgcccgt cacaccatga gagtttgtaa cacccaaagt cggtggggta accttttagg  1440
aaccagccgc ctaaggtatc ga                                           1462
```